United States Patent [19]

Edwards et al.

[11] Patent Number: 4,772,736

[45] Date of Patent: Sep. 20, 1988

[54] PROCESS FOR THE PREPARATION OF ALUMINOXANES

[75] Inventors: David N. Edwards; John R. Briggs; Arthur E. Marcinkowsky, all of Charleston; Kiu H. Lee, South Charleston, all of W. Va.

[73] Assignee: Union Carbide Corporation, Danbury, Conn.

[21] Appl. No.: 124,084

[22] Filed: Nov. 23, 1987

[51] Int. Cl.$^4$ ............................................... C07F 5/06
[52] U.S. Cl. .................................................... 556/179
[58] Field of Search .......................................... 556/179

[56] References Cited

U.S. PATENT DOCUMENTS

| | | | |
|---|---|---|---|
| 2,917,366 | 12/1959 | Hansford | 556/179 X |
| 3,242,099 | 3/1966 | Manyik et al. | 252/429 |
| 3,347,840 | 10/1967 | Manyik et al. | 260/94.9 |
| 4,665,208 | 5/1987 | Welborn et al. | 556/179 |
| 4,668,838 | 5/1987 | Briggs | 585/513 |

FOREIGN PATENT DOCUMENTS 62-148496  7/1987  Japan ................................. 556/179

*Primary Examiner*—Paul F. Shaver
*Attorney, Agent, or Firm*—Saul R. Bresch

[57] ABSTRACT

A process for the preparation of aluminoxanes comprising introducing, under reaction conditions, at least one stream of water beneath the surface of an agitated solution of a hydrocarbyl aluminum compound in such a manner that the stream of water is essentially immediately dispersed on contact with the solution.

12 Claims, 1 Drawing Sheet

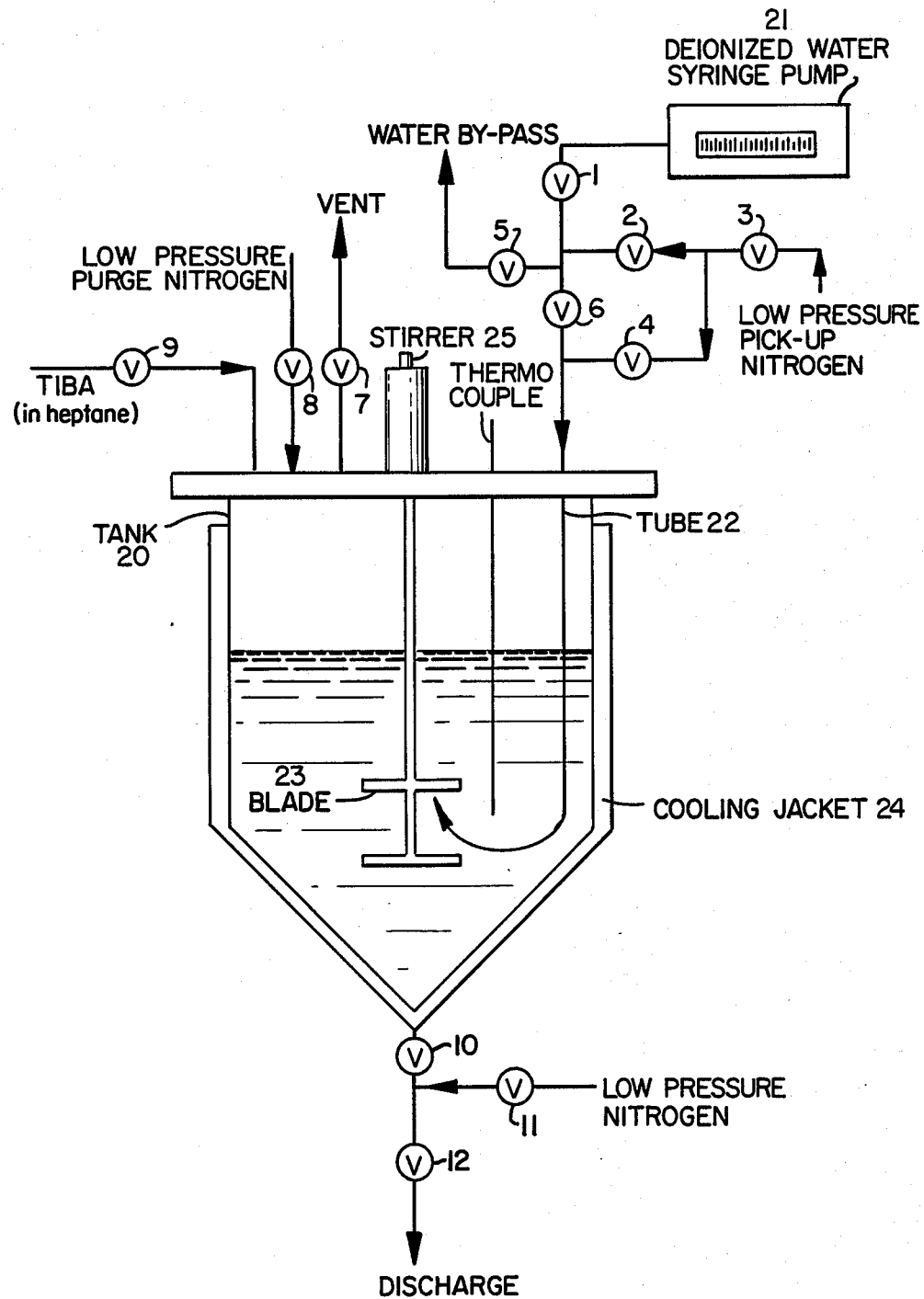

PROCESS FOR THE PREPARATION OF ALUMINOXANES

TECHNICAL FIELD

This invention relates to a process for the preparation of aluminoxanes, which are useful in catalyst systems.

BACKGROUND

Aluminoxanes, made by the incomplete hydrolysis of hydrocarbyl aluminums, find extensive use as alkyl substitutes in Ziegler-Natta catalyst systems and as cocatalysts for ethylene trimerization.

There are two kinds of aluminoxanes: cyclic aluminoxanes, which can be represented by the formula $-[-R-Al-O-]_n$, and linear aluminoxanes, which can be represented by the formula $R-[R-Al-O]-_nAlR_2$.

Synthesis of the cyclic aluminoxane can be described by the following equation:

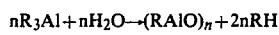

$$nR_3Al + nH_2O \rightarrow (RAlO)_n + 2nRH$$

A typical hydrolysis can be carried out at atmospheric pressure at a temperature in the range of about 0° C. to about 100° C., and preferably at a temperature in the range of about 5° C. to about 15° C. Water is added to a solution of, for example, trialkyl aluminum in an anhydrous, inert organic solvent. The concentration varies from about 5 percent by weight aluminum compound to about 75 percent by weight based on the total weight of the solution. The water is preferably added slowly but in a single batch, with vigorous stirring and cooling. The reaction is considered complete when effervescence ceases.

Another method for preparation of the aluminoxane is accomplished by using the water of hydration of metal salts, e.g. by adding about 0.1 to about 0.16 mole of solid magnesium sulfate heptahydrate to a ten percent solution of triisobutyl aluminum in heptane. The mixture is stirred vigorously until effervescence ceases, usually overnight or even longer.

The solutions are stored under an inert gas such as argon.

Examples of suitable solvents are heptane, hexane, pentane, isooctane, purified kerosene, cyclopentane, cyclohexane, methylcyclopentane, and dimethylcyclopentane. The use of 1-hexene is found to be advantageous in some cases. Benzene, toluene, and xylene can be used, but are not preferred.

Examples of useful hydrocarbyl aluminum compounds are as follows: tri-isobutylaluminum, trihexyl aluminum, isobutyl aluminum dihydride, hexyl aluminum dihydride; di-isobutyl aluminum hydride, dihexyl aluminum hydride, di-isobutylhexyl aluminum, isobutyl dihexylaluminum, trimethyaluminum, triethylaluminum, tripropylaluminum, tri-isopropylaluminum, tri-n-butylaluminum, trioctylaluminum, tridecylaluminum, tridodecylaluminum, tribenzylaluminum, triphenylaluminum, trinaphthylaluminum, and tritolylaluminum. The preferred hydrocarbyl aluminums are tri-isobutylaluminum, trihexyl aluminum, di-isobutyl aluminum hydride, and dihexyl aluminum hydride.

The techniques for the preparation of aluminoxanes should be chosen to ensure that hydrolysis is both uniform and incomplete, the complete hydrolysis product being hydrated aluminum oxide. The undesirable complete hydrolysis is usually the result of localized high water concentrations, typically at water to aluminum mole ratios of about 1.5.

Unfortunately, the prior art methods suffer from these localized high water concentrations, ill-defined hydrolysis ratios so important to ethylene trimerization, resistance to scale-up, and relatively long preparation times, and the problem of waste streams or recycle streams where hydrated salts are concerned.

DISCLOSURE OF INVENTION

An object of the invention, therefore, is to provide a process for the preparation of aluminoxanes which are relatively free from the above enumerated deficiencies. Other objects and advantages will become apparent hereinafter.

According to the present invention, then, a process for the preparation of aluminoxanes has been discovered comprising introducing, under reaction conditions, at least one stream of water beneath the surface of an agitated solution of a hydrocarbyl aluminum compound in such a manner that the stream of water is essentially immediately dispersed on contact with the solution.

More particularly, the process comprises introducing, under reaction conditions, water into an agitated solution of a hydrocarbyl aluminum compound, the water being introduced through at least one tube, the outlet of which is beneath the surface of the solution, wherein:

(i) the solution is agitated with stirring means having at least one blade; and (ii) the outlet of the tube is located in such close proximity to the blade that the shear created by the blade essentially immediately disperses the water as it leaves the outlet.

BRIEF DESCRIPTION OF THE DRAWING

The sole figure is a schematic drawing of an apparatus in which subject process can be carried out.

DETAILED DESCRIPTION

Aluminoxanes, which are also known as alumoxanes, are the reaction product of a hydrocarbyl aluminum compound and water. They are generally polyalkylaluminoxanes, which are derived from polyalkyl aluminum compounds, usually trialkyl aluminum compounds, although, as noted, triaryl aluminum compounds and alkyl aluminum hydrides can be used. The preferred hydrocarbyl aluminum compounds are also mentioned above.

The water is preferably deionized, and distilled water is recommended to avoid introducing impurities into the system. The mole ratio of water to aluminum (hydrolysis ratio), which can be used in the process is maintained in the range of about 0.5:1 to about 1.1:1 and is preferably maintained in the range of about 0.8:1 to about 0.9:1. The optimum is about 0.85:1. These mole ratios are considered to be particularly effective where the aluminoxane is to be used as a cocatalyst in an ethylene trimerization process.

The solvent for the hydrocarbyl aluminum is also of relatively high purity. These solvents are mentioned above. Generally, the hydrocarbyl aluminum compound is present in the solution in an amount of about 5 to about 40 percent by weight based on the weight of the solvent. Preferred solutions are in the range of about 10 to about 20 percent by weight.

The process is conducted in an inert gas environment and the resulting aluminoxane is maintained and stored in the same manner. A batch or continuous mode is used.

Since the reaction is highly exothermic, cooling means are provided to slow down the reaction. The reaction is generally maintained at a temperature in the range of about 5° C. to about 70° C. and preferably in the range of about 5° C. to about 20° C. Reaction pressure is generally kept in the range of about 2 psig to about 10 psig and preferably in the range of about 2 psig to about 5 psig.

The process involves the direct addition of liquid water to a well agitated solution of hydrocarbyl aluminum. The water is introduced through one or more narrow tubes to facilitate its immediate dispersion upon contact with the hydrocarbyl aluminum solution. The diameter of the tubes can range from about ⅛ inch to that of a fine capillary which is usually in the range of about 1/16 to about 1/32 inch. Usually, one tube is adequate to accomplish the task, but, on scale-up, two or three or more tubes can be utilized.

The outlet of the tube is located in close proximity to a blade of the stirring means, which can be an impeller, a stirrer, or other bladed device. The high shearing action of the blade continually sweeps the outlet clean of the water immediately as the water makes its exit. This immediate dispersion avoids or minimizes localized high water concentrations. In order to provide a continual sweep, the flow rate of the water, the number of blades, and the revolutions per minute (RPM) are coordinated. This coordination is well within the skill of a journeyman engineer.

Referring to the drawing:

A typical apparatus for carrying out the process of this invention is shown in the drawing. The apparatus includes glass mix tank 20 surrounded by cooling jacket 24; blade 23 attached to stirrer 25; syringe pump 21 connected to tube 22; and valves 1 to 12, which control the passage of gas or liquid through tube 22 and various unnumbered conduits. A cooling fluid such as mineral oil is circulated through jacket 24 from a cooling bath (not shown). Deionized water is fed to mix tank 20 by syringe pump 21 through ⅛ inch stainless steel tubing 22. The outlet of tube 22 is preferably constructed so that the water is sprayed from tube 22 into the solution. At a point near the tube inlet, low pressure pick-up nitrogen is introduced into the water stream to assist in the spray. The spray is, in turn, introduced beneath the surface of the solution into a well agitated high shear zone adjacent or in close proximity to blade 23, usually at the tip of the impeller blade.

A typical procedure for carrying out the process in conjunction with the apparatus described in the drawing and above is as follows:

The apparatus is purged with nitrogen. Valves 3, 4 and 7 are opened to maintain a continuous nitrogen purge through tube 22 to prevent hydrocarbyl aluminum from entering the tube. The hydrocarbyl aluminum solution is pressure fed to tank 20 through valve 9. Stirrer 25, which has two upper blades and two lower blades, is operated at 450 rpm. Jacket 24 is set to 0° C. The hydrocarbyl aluminum solution is permitted to reach a temperature of 5° to 15° C. De-ionized water is introduced, at 0.1 cubic centimeter per minute, through tube 22 into tank 20 using valves 1, 2, 4, 5, and 6 in open and closed modes. A nitrogen purge through valve 8 is used to strip off, e.g., isobutane, liberated by the reaction of water with tri-isobutyl aluminum. The solution is stirred for one hour at 10° to 25° C., and is then discharged.

Important process variables are the water feed rate; the reaction temperature; the hydrolysis ratio; the redistribution temperature, i.e., the temperature at which the solution is stirred after addition of water; and stirrer speed. The stirrer speed is linked to the water feed rate and the reaction temperature. Water can be added at faster rates by increasing the stirrer speed and/or the number of blades on the stirrer.

The selectivity of a chromium based catalyst prepared with an aluminoxane made in accordance with this invention is illustrated by the following examples.

EXAMPLES 1 to 8

All operations involving the use of catalyst components are conducted under an inert argon atmosphere. Heptane solvent is first stirred over concentrated sulfuric acid for 2 days to remove water, aromatics, and other unsaturates, then stored over and distilled under argon from calcium hydride or a sodium/potassium alloy before use. Heptane can also be purified, e.g., by hydrogenation in the presence of a catalyst and then sieved through a 13-x molecular sieve. Other additives are purified in a conventional manner, e.g., monoglyme is distilled under argon from sodium metal and stored over molecular sieves in the dark. Ethylene is polymer grade. It is purified to polymerization process specifications and further dried by passage through molecular sieves.

Chromium (III) tris(2-ethylhexanoate) is typically prepared from anhydrous chromium (III) chloride and 2-ethylhexanoic acid as follows: About 110 cubic centimeters (cc.) of 2-ethylhexanoic acid is heated to 130° C. and sparged with argon for about 2 hours to drive off any contaminating water. After cooling to 80° C., 11.2 grams of anhydrous chromium (III) chloride is added over a period of 20 minutes. The temperature of the mixture is raised slowly to 230° C. over a period of 6.5 hours before being cooled. The mixture is then stripped under a vacuum of about one millimeter of mercury at 160° C. to drive off unreacted acid and other volatiles. This gives a glassy green solid. The product is extracted from unreacted chromium (III) chloride and other insoluble material with three 100 cc portions of diethyl ether, filtered, and stripped under vacuum.

Triisobutylaluminum is used as received from the manufacturer. A 20 percent by weight solution of triisobutylaluminum in heptane is used to prepare triisobutyl aluminoxane in accordance with the procedure described above. As for this procedure, the preparation is carried out in the apparatus described in the drawing and above.

The aluminoxane solution is added to the chromium (III) tris(2-ethylhexanoate) dissolved in about 50 milliliters of heptane, under argon, in a predried 300 milliliter stainless steel autoclave, followed by the ligand additive to provide a certain mole ratio of ligand to chromium. The autoclave is thoroughly degassed with argon, then, ethylene, and pressurized with ethylene. The autoclave is heated to the desired temperature (see below) and additional ethylene is added to bring the autoclave to the desired final pressure in the range of 400 to 500 psig. As consumption of ethylene lowers the pressure, repressurization is repeated. The rate of ethylene consumption is typically 2000 grams per gram of chromium per hour at about 100° C.

After cooling, excess ethylene is vented, collected, and quantified. The ethylene consumed is determined by weighing before and after the reaction, with unreacted ethylene being determined by venting from the reactor into a liquid nitrogen trap. Volatile products are distilled from the polymer and catalyst residues and determined by gas chromatography using cyclohexane as an internal standard. The polymer cannot be quantified directly since it is contaminated with catalyst residues, but is obtained by difference, and this value is estimated by weighing the polymer and the catalyst residues and subtracting the catalyst residues from the total weight of involatile products. Selectivities are normalized to 100 percent. The components are introduced into the autoclave to provide approximately 0.1 millimole of chromium; 5.0 millimoles of aluminum plus water; an aluminum/chromium mole ratio of 50 to 1; and a ligand additive/chromium mole ratio of about 11. The trimerization is run in approximately 75 milliliters of heptane solvent at a temperature of about 95° C. The temperature is selected to give a suitable reaction rate.

The product obtained contains 1-hexene and polyethylene in a combined total of at least 98 percent by weight based on the weight of ethylene consumed. The balance of the product is represented by undefined octenes, 1-butene, and cis and trans 2-butene.

Variables and results are explained below and set forth in the Table.

1. Water feed rate is the rate at which water is fed in the aluminoxane preparation procedure. The values are given in cubic centimeter per minute.
2. The reaction temperature (in °C.) is the temperature at which the tri-isobutylaluminum/water reaction is maintained in the mix tank.
3. The redistribution temperature (in °C.) is the temperature in step 15 of the aluminoxane procedure.
4. The hydrolysis ratio is, as noted, the ratio of the number of moles of water to the number of moles of aluminum. This ratio is the ratio used in the aluminoxane preparation procedure and, thus, the ratio in the tri-isobutyl aluminoxane used in the trimerization.
5. The amount made is the number of liters of 20 weight percent solution of polyisobutyl aluminoxane in heptane made in the aluminoxane preparation procedure.
6. Selectivity to free 1-hexene is calculated on (i) weight of ethylene consumed or (ii) weight of 1-hexene divided by weight of 1-hexene plus weight of polymer, the quotient being multiplied by 100 percent. The value is given in weight percent.
7. Activity is the pounds of 1-hexene produced per pound of tri-isobutylaluminum per hour.

We claim:

1. A process for the preparation of an aluminoxane comprising introducing, under reaction conditions, at least one stream of water beneath the surface of an agitated solution of a hydrocarbyl aluminum compound in such a manner that the stream of water is essentially immediately dispersed on contact with the solution.
2. The process defined in claim 1 wherein the mole ratio of water to aluminum is maintained in the range of about 0.5:1 to about 1.1:1.
3. The process defined in claim 1 wherein the solvent is a liquid hydrocarbon inert to the hydrocarbyl aluminum compound/water reaction.
4. The process defined in claim 1 wherein the hydrocarbyl aluminum is a trialkyl aluminum, a triaryl aluminum, an alkyl aluminum dihydride, or a dialkyl aluminum hydride.
5. The process defined in claim 2 wherein the mole ratio of water to aluminum is maintained in the range of about 0.8:1 to about 0.9:1.
6. The process defined in claim 3 wherein the hydrocarbyl aluminum compound is present in the solution in an amount of about 5 to about 40 percent by weight based on the weight of the solvent.
7. A process for the preparation of aluminoxanes comprising introducing, under reaction conditions, water into an agitated solution of a hydrocarbyl aluminum compound, the water being introduced through at least one tube, the outlet of which is beneath the surface of the solution, wherein:
   (i) the solution is agitated with stirring means having at least one blade; and
   (ii) the outlet of the tube is located in such close proximity to the blade that the shear created by the blade essentially immediately disperses the water as it leaves the outlet.
8. The process defined in claim 7 wherein the mole ratio of water to aluminum is maintained in the range of about 0.5:1 to about 1.1:1.
9. The process defined in claim 7 wherein the solvent is a liquid hydrocarbon inert to the hydrocarbyl aluminum compound/water reaction.
10. The process defined in claim 7 wherein the hydrocarbyl aluminum is a trialkyl aluminum, a triaryl aluminum, an alkyl aluminum dihydride, or a dialkyl aluminum hydride.
11. The process defined in claim 8 wherein the mole ratio of water to aluminum is maintained in the range of about 0.8:1 to about 0.90:1.
12. The process defined in claim 9 wherein the hydrocarbyl aluminum compound is present in the solution in an amount of about 5 to about 40 percent by weight based on the weight of the solvent.

TABLE

| Example | Water Feed Rate (cc/min) | Reaction Temp. (°C.) | Hydrolysis Ratio (Mole) | Redistribution Temp. (°C.) | Amount Made (Liters) | Selectivity (wt. %) | Activity (lb/lb cat/hr) |
|---|---|---|---|---|---|---|---|
| 1 | 0.11 | 7 | 0.80 | 10 | 2.5 | 65 | 98 |
| 2 | 0.11 | 10 | 0.85 | 12 | 1.5 | 81 | 66 |
| 3 | 0.11 | 14 | 0.85 | 13 | 1.5 | 72 | — |
| 4 | 0.11 | 13 | 0.83 | 15 | 1.5 | 79 | 49 |
| 5 | 0.11 | 16 | 0.85 | 14 | 1.5 | 75 | 39 |
| 6 | 0.11 | 12 | 0.85 | 12 | 1.5 | 74 | 50 |
| 7 | 0.11 | 16 | 0.83 | 13 | 1.5 | 78 | 50 |
| 8 | 0.11 | 16 | 0.85 | 15 | 1.5 | 75 | 52 |

* * * * *